(12) United States Patent
Matthews et al.

(10) Patent No.: US 8,457,709 B2
(45) Date of Patent: Jun. 4, 2013

(54) SENSOR MOUNTING SYSTEM

(75) Inventors: Robert Matthews, San Diego, CA (US);
Neil John McDonald, San Diego, CA (US)

(73) Assignee: Quantum Applied Science & Research, Inc., San Diego, CA (US)

( * ) Notice: Subject to any disclaimer, the term of this patent is extended or adjusted under 35 U.S.C. 154(b) by 1382 days.

(21) Appl. No.: 12/153,659

(22) Filed: May 22, 2008

(65) Prior Publication Data
US 2009/0030298 A1    Jan. 29, 2009

Related U.S. Application Data

(60) Provisional application No. 60/924,638, filed on May 23, 2007.

(51) Int. Cl.
*A61B 5/04*   (2006.01)

(52) U.S. Cl.
USPC ............ 600/383; 600/372; 600/393; 600/544

(58) Field of Classification Search
USPC ................ 600/372–373, 382–390, 509, 544, 600/547; 607/142
See application file for complete search history.

(56) References Cited

U.S. PATENT DOCUMENTS

| 4,709,702 A * | 12/1987 | Sherwin .......................... 600/383 |
| 4,967,038 A | 10/1990 | Gevins et al. |
| 5,038,782 A | 8/1991 | Gevins et al. |
| 5,511,546 A | 4/1996 | Hon |
| 5,564,433 A * | 10/1996 | Thornton ....................... 600/544 |
| 6,161,030 A * | 12/2000 | Levendowski et al. ........ 600/383 |
| 6,491,647 B1 * | 12/2002 | Bridger et al. ................. 600/585 |
| 6,510,333 B1 * | 1/2003 | Licata et al. ................... 600/383 |
| 6,732,592 B1 | 5/2004 | Blackburn et al. |
| 6,961,601 B2 | 11/2005 | Matthews et al. |
| 2002/0177767 A1 | 11/2002 | Burton et al. |
| 2007/0225585 A1 | 9/2007 | Washbon et al. |
| 2007/0235716 A1 | 10/2007 | Delic et al. |
| 2007/0238945 A1 * | 10/2007 | Delic et al. .................... 600/383 |
| 2009/0156925 A1 * | 6/2009 | Jin et al. ......................... 600/396 |
| 2009/0253996 A1 * | 10/2009 | Lee et al. ....................... 600/544 |
| 2010/0198042 A1 * | 8/2010 | Popescu et al. ............... 600/383 |

* cited by examiner

*Primary Examiner* — Linda Dvorak
*Assistant Examiner* — Brian M Antiskay
(74) *Attorney, Agent, or Firm* — Diedericks & Whitelaw, PLC

(57) ABSTRACT

A sensor mounting system includes a rigid main body portion defining a housing within which is mounted a compression element. In use, the compression element provides a predetermined biasing force to force a sensor against the skin of a subject. A secondary support structure provides an adjustable biasing force to retain the main body portion against the subject. Alternatively, the main body portion may be mounted to a rigid pod with one or more secondary compression elements, with the pod itself retained against the subject. An interface layer extending from the main body portion provides a cushion to improve the comfort of the subject. The interface layer and sensor interface elements may be in the form of fingers to increase contact of the sensor with a selected portion of the subject.

24 Claims, 5 Drawing Sheets

SENSOR MOUNTING SYSTEM

CROSS-REFERENCE TO RELATED APPLICATIONS

The present application claims the benefit of U.S. Provisional Patent Application Ser. No. 60/924,638 entitled "Wearable Bioelectrode" filed May 23, 2007.

STATEMENT REGARDING FEDERALLY SPONSORED RESEARCH AND DEVELOPMENT

This invention was made with Government support under Contract No. W91ZKL-04-P-0235 awarded by NAVAIR. The Government has certain rights in the invention.

BACKGROUND OF THE INVENTION

The present invention generally pertains to holding a sensing device against a person or animal. More particularly, the present invention pertains to sensing devices for which the performance depends at least partly on the contact pressure of the device to the body. The present invention is particularly, but not exclusively, useful for long duration measurement of biopotentials on the skin.

There are many current and emerging technologies that require contact between a sensing device and a living person or animal. In many cases, the performance of the device depends on the pressure that is used to hold the sensing device against the subject. Examples include sensors that measure biopotentials, sensors that record temperature or sound, and thermoelectric generating devices that produce electrical power via heat conducted from the skin. In all cases a tradeoff is made between the discomfort that arises due to the pressure holding the sensor against the body and the quality of the electrical, thermo, acoustic, or other coupling.

In the specific case of biopotential sensors, the standard practice is to utilize a conducting electrolyte, typically a gel, between the part of the sensor that collects the signal (often termed the electrode) and the skin. The gel provides a low impedance electrical contact which allows relatively simple amplification electronics to be used. In addition, the fluid nature of the gel allows the electrode to move slightly away from the subject without breaking electrical contact, thereby reducing the pressure that is required to ensure a reliable coupling of the signal. Similar gels can be employed to improve thermal and acoustic contact. Application of gels is currently the standard method used in clinical and research biopotential measurement applications due to the relatively low cost of the electrode and gel, their relatively long history of use, and the fact that the technique requires only a low level of training to ensure the electrodes have reliable coupling. There are, however, certain disadvantages with this technique. Specifically, the gels begin to cause skin irritation and become uncomfortable after about one day of use, limiting the capability for long-term biopotential recording. Further, a large amount of gel is needed when hair is present, or the subject must be shaved, which is both time and manpower intensive and unpleasant for the subjects. In addition, gels or other conducting fluids dry out and must be replaced. Because of these limitations, biopotential measurements are typically performed by trained staff in clinical settings, on partly unclothed subjects, for short periods of time.

An alternative type of biopotential sensor utilizes a surface electrode that does not require an electrolyte fluid or gel. These electrodes are referred to as dry electrodes and typically employ an impedance transformation using active electronics to accommodate the high impedance electrical contact that is made to the skin when fluids are not used. Typically, a dry electrode is a conductive material which is placed in direct contact with the skin and relies on a combination of resistive and capacitive coupling to the local skin potential to receive its signal. More recently, dry electrodes that rely entirely on capacitive coupling to the local skin potential have been developed. Dry electrodes offer considerable benefits in ease of use, comfort and the capability for long-term operation over many days to monitor chronic disease and health status of workers in hazardous environments.

Heretofore, active dry and insulated electrodes have not typically exhibited the same consistency and signal-to-noise ratio (SNR) as wet electrodes. In particular, dry electrodes are strongly affected by small displacements away from the skin. For dry electrodes with a conducting surface, the signal is mostly lost if the electrode is moved away from the skin by only a few microns. For capacitive electrodes, the coupling is proportional to the inverse of the separation distance between the sensor and the skin. In numerical terms, the coupling is typically reduced by a factor of about 10 as the electrode moves from a position of contact with the skin to a stand-off distance of only about 100 µm. This sensitivity to small displacements has largely prevented the use of dry biopotential electrodes.

Biopotential and also thermal and acoustic coupling is typically affected by bone and tendons in the immediate vicinity. As a result, such signals are typically gathered from areas of skin adjacent to soft tissue. Given the inherent pliable nature of soft tissue and variations in local body curvature, it is difficult to make reliable physical contact. Further, when subjects move, inertial forces can act to pull the sensor away from the skin. Thus, it is difficult to ensure reliable coupling of a sensor for detection of the variable of interest (potential, temperature, sound etc.) without applying a large force to ensure the sensor is held against the subject. However, application of pressure to the skin, particularly on the head, can quickly lead to intolerable discomfort. Thus, there immediately arises a trade-off between comfort due to the contact pressure of the sensor on the skin and the quality of the physical contact. This trade-off is particularly difficult to make for dry biopotential electrodes owing to their greater sensitivity to displacement from the skin.

The standard method to mount biopotential electrodes and most other sensors is to stick them to the skin using an adhesive, thereby avoiding the need to apply pressure. In standard clinical settings, the adhesive is typically no more uncomfortable than the electrolyte, and patients with a large amount of hair are often shaved, which helps the adhesive to attach. Further, if the adhesive contact breaks, technicians are generally on hand to reattach the electrode, and the recordings are less than a day in duration so the requirements for adhesive durability are not severe. However, one of the principal goals of using dry electrodes is to provide the capability for comfortable, long-term biopotential recordings. Another is to enable a system that can simply be put on as an item of clothing. Using an adhesive to hold the sensors in place runs counter to both of these goals. Therefore, to realize the benefit of a dry electrode, a system and method is needed to hold the electrode against the subject in an adequate, reliable pressure controlled way that does not lead to discomfort. A system and method that could provide this capability would have application to other sensors and other instances in which a mechanical interface to the skin is desired.

An alternate way to hold sensors in place against the body is to employ a strap or set of straps that encircle the torso, head or limbs. These straps contain elasticized sections so that they are in tension when in use. Generally, the straps come in a range of sizes or include an adjustable section so that the tension can be set within a desired range regardless of the size of the subject. Simple mechanics means that the tension force, t, in the straps is predominantly parallel to the surface of the body while the component of the force normal to the body is a small fraction of t. To produce an appreciable force normal to the body in order to hold a sensor against the skin, it is necessary to locally deform the straps so that, in the vicinity of each of the sensors, the straps bend away from the body, thereby producing a force in the normal direction. The magnitude of this force depends strongly on the local curvature of the body, making it difficult to set accurately in advance. Secondly, as the strap system is put on, it is difficult to ensure that the relatively large lateral forces present in the straps exactly cancel at each sensor. The resulting unbalanced force is transferred to the sensor, which in turn produces a shear force on the body that is amplified in its discomfort impact on the subject by the relatively small size of the sensor. Further, in the case of biopotential measurements, shear forces stretch the skin, which can create electrical recording artifacts via the piezo electric properties of the skin. In addition, the combination of the unbalanced tension force at the outside of the sensor and the shear force where it touches the body causes a tipping force that can compromise the desired sensor coupling to the body. These inherent problems with strap-based methods have limited their widespread adoption.

A further method to hold sensors in place against the body is to mount the electrode at the end of a sliding mechanism and use a compressed spring to provide a force to push the sensor against the subject. A defect of this approach is that the fixed end of the spring itself must be attached relative to the subject by some means. Such means need a level of flexibility in order to be comfortable and to accommodate the range of subject sizes and subject movement when in use. Thus, the spring that pushes the sensor towards the subject is itself anchored to the subject by a structure that is in some way elastic (e.g., the straps described above). Tension forces in the mounting structure act to oppose the compression force in the spring, reaching an equilibrium when they are equal. The result is that the force applied to hold the sensor against the subject is equal to the component of the tension normal to the body, which is difficult to control, as described above.

One way to minimize discomfort due to lack of control in producing a normal force when holding the sensor against the subject is to make the sensing surface itself mechanically compliant. In the case of biopotential sensors, electrically conducting rubber and foam infused with a conducting fluid has been used. However, utilizing a compliant material typically requires a compromise in the quality of the desired physical coupling and, generally, does not provide sufficient control of the applied pressure. For example, simply contacting the skin by a rubber pad still allows shear forces to be transferred to the skin in the immediate vicinity of the measurement.

In light of the above, it is an object of the present invention to provide a mounting method in which a controlled force is established to hold a sensor against the skin. The magnitude of the force of the sensor against the skin can be set to provide the optimum trade-off between discomfort experienced by the subject and the pressure necessary to provide adequate coupling for the sensor to operate as required. It is a further object of the present invention that the force should be fixed at the time of manufacture, and need not be adjusted for each subject to account for variations in body size and shape. It is yet another object of the present invention that the applied force does not change significantly due to the typical variations in body curvature between subject and variations in curvature that arise during normal bodily movement (e.g., breathing and walking).

SUMMARY OF THE INVENTION

The present invention is directed to a sensor mounting system enabling the placement of a sensor against a subject with a controlled contact pressure. The mounting system includes a sensor and a main body portion that, in general, surrounds the sensor. Both the sensor and the main body portion contact the surface of the subject (e.g., the skin or scalp). A compression element is connected at one end to the sensor, and at the other end to the main body portion, such that the sensor is centered within the main body portion and pressed against the subject by the compression element.

The main body portion is rigid and provides an enclosure within which the sensor can move. The main body portion itself is held against the subject by a secondary mechanism such as a set of elasticized straps or a spring loaded arm. The main body portion further comprises an interface element or layer adapted to contact the subject. The height of the main body portion is chosen so that, for a typical variation in curvature of the subject, the fraction change in length of the compression element is small. Preferably, the interface layer spaces the main body portion from the subject by approximately 1 cm, in order to provide an adequate compression zone for the compression element.

The height of the mount, the mean length of the compression element and the force applied by the compression element at its mean level of compression are all set in advance. Thus, a particular feature of the present invention is that the sensor contact pressure can be accurately specified for the particular part of the body with which the sensor is to be in contact and for the particular range of expected subject activities. This control enables the trade-off between sensor comfort and sensor performance to be optimized and set in advance to a much higher level of fidelity than has previously been possible.

In one preferred embodiment, the sensor is a biopotential sensor that utilizes a dry electrode. The compression element provides a nearly constant force that holds the electrode against the skin of the subject. Friction where the mount contacts the subject mechanically stabilizes the region of skin or scalp that is enclosed within the footprint of the mount, limiting the stretching that can lead to electrical measurement artifacts. The sensor is held against the scalp by a biasing force that is preset depending on the duration it is to be worn and the level of physical activity expected. Optionally, the surface of the sensor includes fingers that fit between strands of hair, thereby allowing a good contact on subjects with a large amount of hair.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DETAILED DESCRIPTION OF THE PREFERRED EMBODIMENTS

Figure 1:
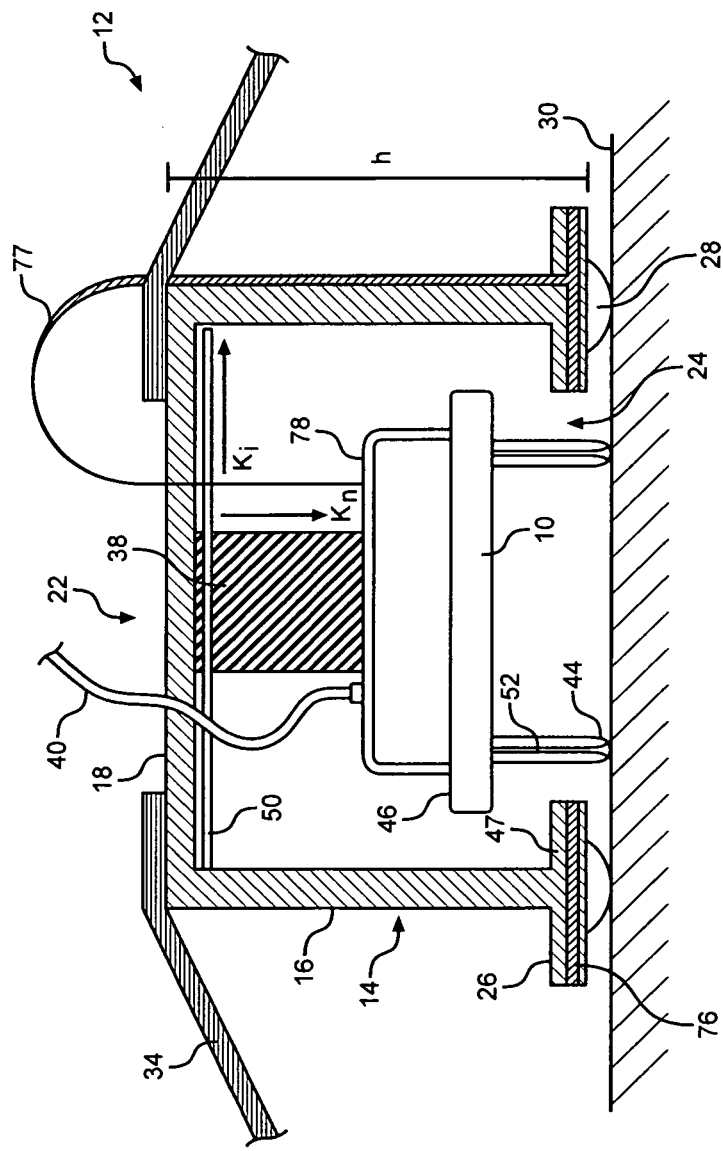
FIG. 1 is a cross-sectional view of a first embodiment of a sensor mounting system of the present invention.

With initial reference to FIG. 1, a sensor mounting system for optimally coupling a sensor 10 to a living subject is shown and generally designated 12. Mounting system 12 includes a main body portion 14 having at least one side wall 16 and a top wall 18, which together define a housing 22 having an opening 24. In a preferred embodiment, main body portion 14 is in the form of a short cylinder including extension stops 26 extending therefrom and having an interface layer 28 that forms the predominant contact to a surface 30 (i.e., skin) of a living subject. A secondary support structure 34 provides a mechanical force that holds mounting system 12 to surface 30. Secondary support structure 34 can be straps, or other means might be used, such as a spring arm or an item of clothing for supporting and positioning mounting system 12. Further, the connection between main body portion 14 and secondary support structure 34 can be made at two fixed points, as shown in FIG. 1, at three or more fixed points, or can be in the form of a pivot or sliding mechanism (not shown). The contact pressure or force of main body portion 14 against surface 30 is determined by secondary support structure 34 and can be adjusted by a user. Accordingly, interface layer 28 is designed for maximum comfort and can be made from soft rubber, foam, or fabric. In addition, the surface area of main body portion 14 in contract with surface 30 can be increased as desired to minimize contact pressure. The interface between main body portion 14 and surface 30 has only to be designed for comfort and reliable seating against surface 30, and does not also have to couple to or transfer a physical variable, such as electric potential, electric current, temperature or sound, into a recording system.

Inside housing 22, sensor 10 is connected to top wall 18 of main body portion 14 by a compression element 38, which acts to bias sensor 10 in the direction of opening 24 and against surface 30 of the subject. Sensor 10 is preferably a wet or dry biopotential sensor, but can also be a thermal sensor, an acoustic sensor, or any other type of sensor that can collect data from the surface of a living subject. For example, included under the term sensor are thermoelectric generators or electrical conductors that produce electrical power by conducting heat from the skin of a living subject. In a preferred embodiment shown, sensor 10 contacts surface 30 via sensor interface element 44. The output of sensor 10 is shown as being carried by an output cable 40, although wireless transmission can also be utilized. Additionally, output cable 40 could carry power and/or a voltage reference to sensor 10.

Tension applied by secondary mounting structure 34 presses interface layer 28 against surface 30. Preferably, interface layer 28 spaces main body portion 14 from the subject by approximately 1 cm in order to provide an adequate compression zone for compression element 38. Main body portion 14 is rigid, thereby providing a well controlled height h when in operation for compression element 38. More specifically, main body portion 14 provides a housing 22 having a consistent height, h, within which compression element 38 may extend and retract. Height h is chosen so that, for a typical variation in curvature of surface 30 of the subject, the fraction change in length of compression element 38 is small. For example, when moving across the scalp a lateral distance of 1 cm, the deviation from the average scalp surface elevation for typical subjects is approximately ±1 mm. For a suitable preloaded compression element, a ±1 mm change in extension need only represent a few percent deviation in natural length with a corresponding change in applied biasing force. Thus, the extension of main body portion 14 away from the subject implemented according to the invention minimizes the variation in contact pressure due to natural variations in surface curvature between subjects.

Variations in subject surface curvature also occur on a constant basis due to normal bodily functions (e.g., breathing, heart beat) and also when the subject moves (e.g., turning, walking, running). In the former case, the surface variations are small, intermittent and frequent. The latter results in much larger surface variations, but their occurrence is much less frequent. In both cases the capability afforded by mounting system 12 to minimize the change in sensor contact pressure resulting from such surface variations greatly reduces the discomfort in wearing sensor 10 and, thereby enables new modalities in which sensor 10 can be worn for long periods of time and under a wide range of subject activities.

Compression element 38 may be an elastic medium, such as a loosely wound mechanical spring or soft foam, for example. Compression element 38 has a weak spring constant, preferably about 1 g/mm to 5 g/mm, in order that the absolute change in compression force exerted by compression element 38 changes by only a small amount when sensor 10 is displaced from its average position by variations in the local shape of surface 30, against which sensor 10 is seated in an operable position. Minimizing the change in force that occurs due to these natural variations allows the contact pressure between sensor 10 and surface 30 to be controlled more accurately.

In order to produce an adequate average sensor-to-subject contact force when mounting system 12 is placed against surface 30 of the body, compression element 38 is maintained in a net state of compression when not in use by extension stops 26. More specifically, compression element 38 biases sensor 10 toward opening 24, and end portions 46 of sensor 10 abut an inside portion 47 of extension stops 26 to prevent sensor 10 from extending beyond housing 22. When mounting, system 12 is placed on a subject, sensor 10 is pushed back from extension stops 26 by a predetermined distance, thereby providing a desired contact pressure. If compression element 38 was not preloaded, sensor 10 would have to extend well beyond main body portion 14 in order to be compressed by a sufficient amount to produce the required force in compression element 38 at the desired operating point. However, experience shows that if sensor 10 extends well beyond main body portion 14 or, more particularly, interface layer 28, then it becomes difficult to place mounting system 12 on a subject in the easy manner provided by the present invention.

The amplitude of the force applied by compression element 38 is preset to provide the optimum balance between the comfort of a subject and the coupling properties of sensor 10 and interface element 44 for a specific application. One way to produce the desired force is to select compression element 38 on the basis of its elastic constant. In the case of a spring for example, the elastic constant is preferably varied by selecting a base material with the desired elastic modulus and adjusting the cross section of the wire used in the spring and the spring diameter.

The height, h, of housing 22 of main body portion 14 is set to accommodate the thickness of sensor 10 and interface element 44, the compressed length of compression element 38, and the expected variation in the shape of surface 30 where mounting system 12 is intended to be located. Height h can be increased in order to accommodate a wider variation in subject shape, for example when used on different parts of the body. Preferably, there is a small gap between the outer edge of sensor 10 and the inner surface or side wall 16 of main body portion 14 to allow sensor 10 to move laterally and to tilt within housing 22. Allowing sensor 10 to move laterally limits the build up of lateral stress in the skin or scalp immediately below sensor 10. Such stress can lead to stretching of the skin or scalp that is uncomfortable and, moreover, can lead to spurious electrical signals due to the piezo-electric properties of the stratus granulosum layer of the skin. Allowing sensor 10 the freedom to tilt enables it to better follow the local surface curvature of surface 30, providing a more reliable and higher area of contact.

Compression element 38 also serves to mechanically isolate sensor 10 from main body portion 14 during accelerations of the subject. This is important in cases when an acceleration results in main body portion 14 and sensor 10 moving relative to one another. Such relative motion results in a change in compression in compression element 38. The outcome of such a change depends on the frequency of the acceleration and the resonant frequency $\omega_0$ of compression element 38 of sensor mounting system 12, where $\omega_0 = \sqrt{k/m}$, in which k is the spring constant of the material comprising compression element 38 and m is the mass of sensor 10. For accelerations at frequencies above $\omega_0$, compression element 38 attenuates the motion of sensor 10.

For accelerations at frequencies below $\omega_0$ in the direction normal to surface 30 of the subject, compression element 38 does not attenuate the motion of sensor 10. However, for accelerations at frequencies below $\omega_0$ in the direction parallel to surface 30 of the subject, the situation is more complex, because friction between main body portion 14 and surface 30, and between sensor 10 and surface 30, prevents motion until the force parallel to surface 30 of the body exceeds the frictional force. In this case, compression element 38 again serves to provide mechanical isolation for accelerations below $\omega_0$.

In both cases (below $\omega_0$ and above $\omega_0$) it is preferable to have a low value for the spring constant of compression element 38 in order to improve mechanical isolation. However, doing so compromises the force holding sensor 10 against surface 30. This compromise can be alleviated by compressing, or preloading, compression element 38 in the direction normal to surface 30 in order to provide sufficient force to maintain sensor contact with surface 30 for all anticipated motion of mounting system 12. Alternatively, the elastic properties of compression element 38 can differ in the normal (Kn) and parallel ($K_L$) directions or spring constants. In general, the combined mass of sensor 10 and interface element 44 is sufficiently small such that: a) inertial forces horizontal to the surface of the body are less than the frictional force between sensor 10 and surface 30 and b) inertial forces perpendicular to surface 30 are less than the force applied by compression element 38. If either of these conditions is not met then, in the example of mounting system 12 held against a subject's chest, sensor 10 will not remain in a fixed position but will slide down the subject's torso under the influence of gravity, or will lift away from the body if the subject suddenly comes to a stop after a forward motion.

Figure 2:
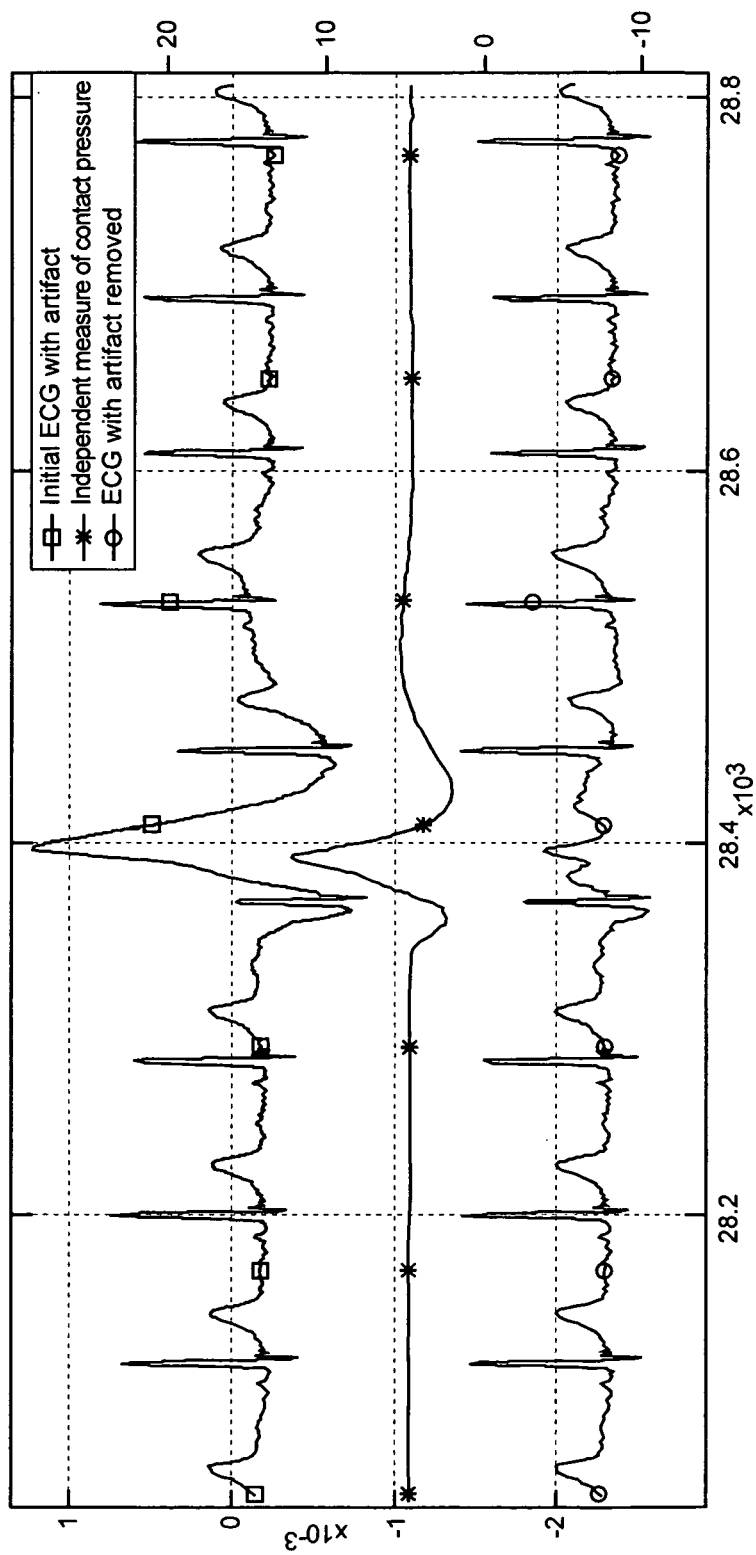
FIG. 2 is a graphical representation of motion artifact cancellation utilizing data from the sensor mounting system of FIG. 1 utilizing a force sensing element.

If desired, a force sensing element or secondary sensor 50 can be incorporated into mounting system 12 as shown in FIG. 1. Preferably, force sensing element 50 records the normal force, $f_n$, and or lateral force, $f_l$, exerted by compression element 38 on main body portion 14. These forces are the vector sum of the contact force, $f_c$, between interface element 44 and surface 30 and the total inertial forces acting on compression element 38, sensor 10 and interface element 44. Preferably, contact force $f_c$ is larger than the total inertial force and so $f_n$ and $f_l$ provide an accurate representation of $f_c$. The representation of $f_c$ so recorded can be inputted into a cancellation algorithm to reject electrical recording artifacts caused by relative motion between interface element 44 and surface 30. A graphical example of the cancellation of such a motion artifact is shown in FIG. 2.

Alternatively, for the case where sensor 10 is a biopotential electrode, a measure of the relative motion between interface element 44 and surface 30 can be gained by monitoring changes in the electrical impedance between sensor 10 and surface 30. Because of the essentially constant, controlled and reliable pressure applied by the invention, changes in impedance can be reliably related to changes in the quality of coupling. Yet another way to monitor small changes in the contact pressure is to incorporate a distance measuring device or displacement sensor indicated at 52, such as a small laser interferometer, into interface element 44. In FIG. 1, displacement sensor 52 is shown touching surface 30, but some forms of sensor 52 may operate without being in contact with surface 30. Such a measurement device records changes in displacement of surface 30 in the vicinity of interface element 44 thereby proving a measure of the force pressing against surface 30, and whether interface 44 slides relative to surface 30. As for the pressure and impedance data, such recordings can be used to identify and reduce the presence of motion induced artifact in the sensor output using processing methods known to this skilled in the art.

For long-term operation it is preferable to use lower values of applied pressure than for short-term operation. This is because it is generally true that the level of comfort decreases as the pressure increases. However, for biopotential measurements, it is observed that at the pressures typically required to get adequate coupling, electrical noise produced by the skin decreases as the pressure increases. The trade-off, therefore, is that long-term measurements of biopotential signals will typically possess a slightly higher level of skin noise than short-term measurements. For thermal and acoustic coupling, similar secondary effects apply depending on the application.

Interface element 44 is in general optimized for the specific type of signal to be carried. For example, for biopotential measurements, interface element 44 can be in the form of a fluid, gel or hydrogel. Preferably, for a biopotential measurement, interface element 44 is a dry electrode that measures the subject potential via resistive and/or capacitive coupling. For a thermal or acoustic measurement, interface element 44 is a material chosen for coupling heat or sound. The shape of interface element 44 depends on where it is intended to be placed on the subject. For a sensor 10 intended for use on a subject's torso, the most suitable geometry will be a flat surface to maximize the coupling area between the subject and sensor 10.

Figure 3:
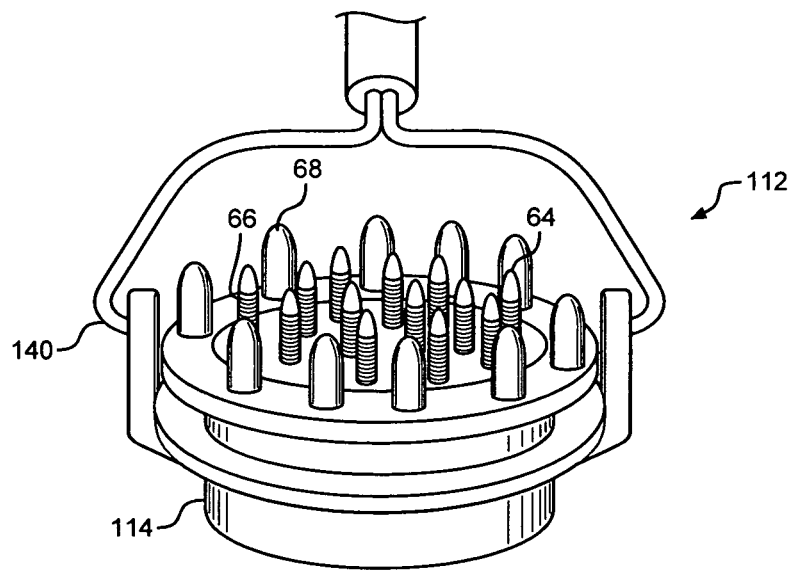
FIG. 3 is a bottom perspective view of the sensor mounting system of FIG. 1.
Figure 4:
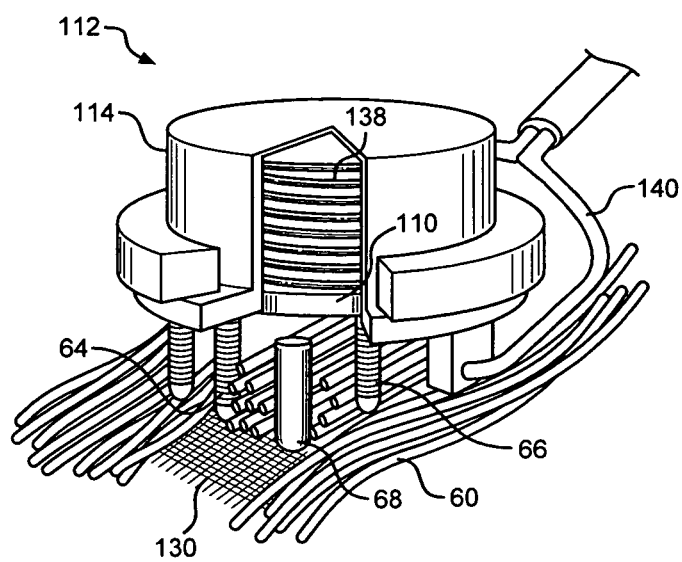
FIG. 4 is a perspective side view of an alternative sensor mounting system of the present invention including fingers that fit through hair on a scalp surface.

A second embodiment of the present invention will now be discussed with reference to FIGS. 3 and 4. In a manner similar to the first embodiment, a mounting system 112 includes a sensor 110 connected to a main body portion 114 by a compression element 138, shown in the form of a spring. Mounting system 112 also includes a wire 140 for communicating information from sensor 110. When the present invention is intended to be utilized with a skin surface 130 including hair 60, such as a scalp surface, the interface element utilized is preferably in the form of fingers 64 that fit through hair 60. Such fingers 64 preferably have rounded tips with a diameter of 1 mm-2 mm, though other cross sections are possible. Experiments have shown that fingers 64 of such size are small enough that they can be put on without trapping hair 60 beneath them. Preferably, the length of fingers 64 is approximately 5 mm-8 mm in order to reach surface 130 through typical layers of hair 60, as depicted in FIG. 4. Additionally, the spacing between fingers 64 is preferably approximately 1 mm-3 mm so that hair 60 can be swept between them. The ends of fingers 64 are smooth for comfort and to prevent scratching of surface 130. Again, the ends can be rounded or include a taper to facilitate parting of hair 60. The sides of fingers 64, i.e., the parts not in contact with surface 130, are preferably covered with an insulating layer or coating indicated at 66 to minimize the pickup of electrical and/or thermal noise and to minimize corrosion on the surface of fingers 64. In the preferred case of a biopotential measurement, the electrical noise measured from the subject's skin or scalp surface 130 is proportional to the inverse square root of the contact area of fingers 64 with surface 130. The number of fingers 64 used therefore is a trade-off between the acceptable level of subject skin noise and the maximum acceptable lateral size of sensor 10, the latter being determined by both the area of each finger 64 and the spacing between fingers 64. The size of sensor 10 is limited by the need to conform to the surface curvature of surface 130. For the case of a dry biopotential measurement, 10-20 fingers 64 are found to be optimal for a sensor diameter of 10-15 mm.

For use on a region with significant hair 60 it is also beneficial to utilize an interface layer in the form of fingers 68, so that it too can fit between individual hairs 60. An example of such fingers 68 is depicted in FIGS. 3 and 4. In this case, fingers 68 are preferably made from a material that is mechanically compliant and has a high coefficient of friction with the skin or scalp surface 130. The dimensions of fingers 68 can be chosen based on the resulting comfort and ease of use only.

Figure 5:
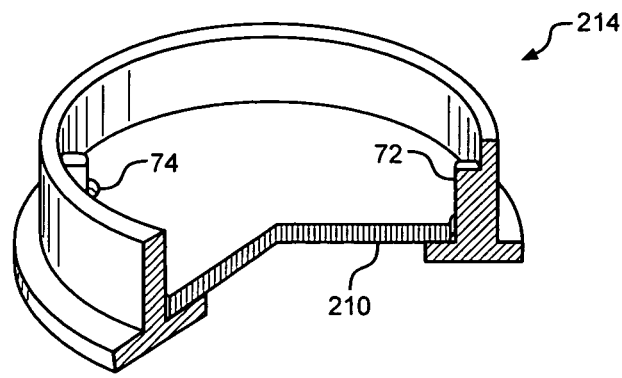
FIG. 5 depicts a means for transferring torque of the present invention.

To seat sensor 110 against surface 130 of the subject, particularly when it is used on a scalp surface 130 or a region of the body with significant hair 60, it is beneficial to be able to rotate sensor 110 back and forth by a small net rotation in order to work fingers 64 and 68 so that they part hair 60, and are thereby positioned closer to the subject surface 130, as shown in FIG. 4. Because sensor 110 is largely or completely enclosed by main body portion 114, it cannot be directly accessed by hand. Compression element 138 is in general too elastic to allow a rotation to be transferred from main body portion 114 to sensor 110. Therefore, in an alternative embodiment shown in FIG. 5, a means is provided for transferring torque between an alternative main body portion 214 and a sensor 210. More specifically, ridges 72 are included within main body portion 214 and extend into slots 74 in the circumference of sensor 210, thereby transferring a rotation force from main body portion 114 to sensor 210. The connection between slots 74 and ridges 72 is sufficiently loose to enable sensor 210 to move laterally and longitudinally within main body portion 214, and also to tilt within main body portion 214.

Figure 6:
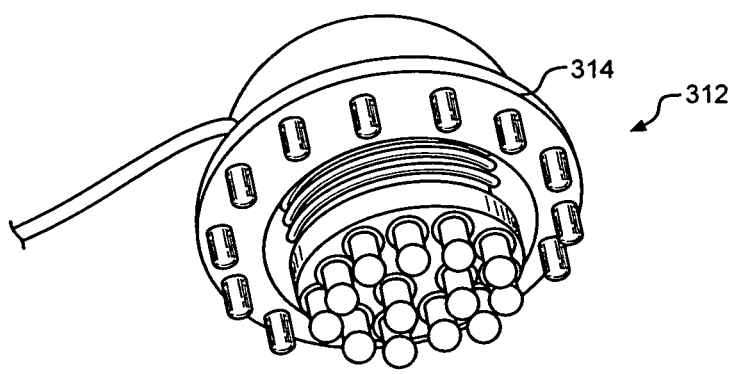
FIG. 6 is a perspective view of a sensing mounting system of the present invention including an electrically insulated main body portion.

In a preferred embodiment in which sensor 10 is a biopotential sensor, it is beneficial to incorporate a metallic conductor or shield 76 with main body portion 14, as shown in FIG. 1. This shield 76 can be connected to sensor 10 via a wire 77 in order to bias it at the same potential as a metal cover 78 used to shield sensor 10 from interference. Shield 76 can thereby be set to the local ground potential or controlled by feedback to be at an optimal potential in a manner known in the art, such as described in U.S. Pat. No. 6,961,601 to Matthews et al. which is incorporated herein by reference. In order to protect the subject from the voltage applied by wire 77, shield 76 can be fully embedded in main body portion 14, and main body portion 14 can be made of an electrically insulating material. This configuration can be seen in an alternative embodiment of the present invention depicted in FIG. 6 wherein a mounting system 312 includes an electrically insulated main body portion 314.

Figure 7:
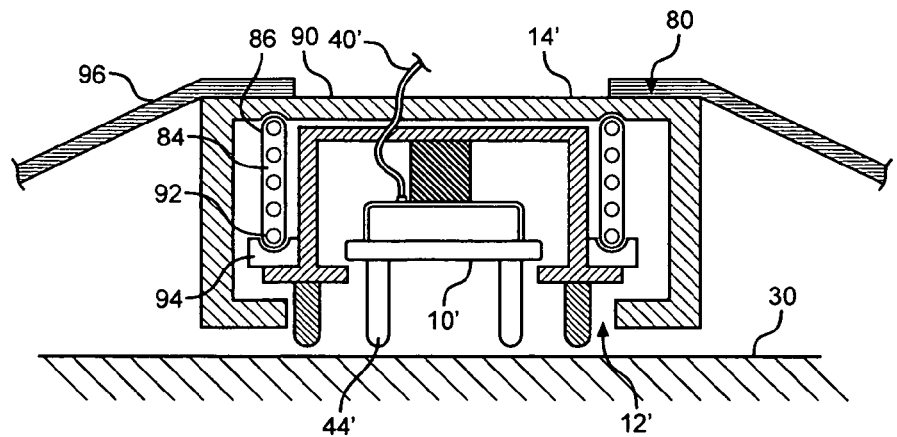
FIG. 7 is a cross-sectional side view of another alternative sensor mounting system of the present invention housed within a mounting pod.

In yet another embodiment of the present invention depicted in FIG. 7, a mounting system 12' similar to the embodiment shown in FIG. 1 is shown incorporated into a rigid mounting pod structure 80, as shown in FIG. 7. Mounting system 12' includes a sensor 10' mounted to a top wall 18' of a main body portion 14' by a compression element 38'. A wire 40' communicates signals from sensor 10', and interface element 44' extends from sensor 10' for contact with surface 30. In this alternative embodiment, sensor 10' is connected to pod 80 by a secondary compression element 84, depicted as a spring in FIG. 7. More specifically, secondary compression element 84 includes a first end 86 that attaches to a top wall 90 of pod 80 and a second end 92 that attaches to a flange 94 extending from main body portion 14'. Pod 80 is held against the subject by a secondary support structure in the form of straps 96. Pod 80 provides isolation between straps 96 and mounting system 12. The longitudinal and lateral spring constants of secondary compression element 84 are established in an equivalent manner to those for compression element 38 discussed with reference to FIG. 1. Advantageously, pod 80 reduces the transfer of sudden longitudinal and lateral forces from the subject to mounting system 12'. This isolation allows a reduction in the force used to hold mounting system 12' to the subject and thereby improves the trade-off between comfort and sensor coupling performance. In particular, pod 80 allows collection of low amplitude biopotential signals such as electroencephalogram (EEG) signals from a subject who is running.

Figure 8:
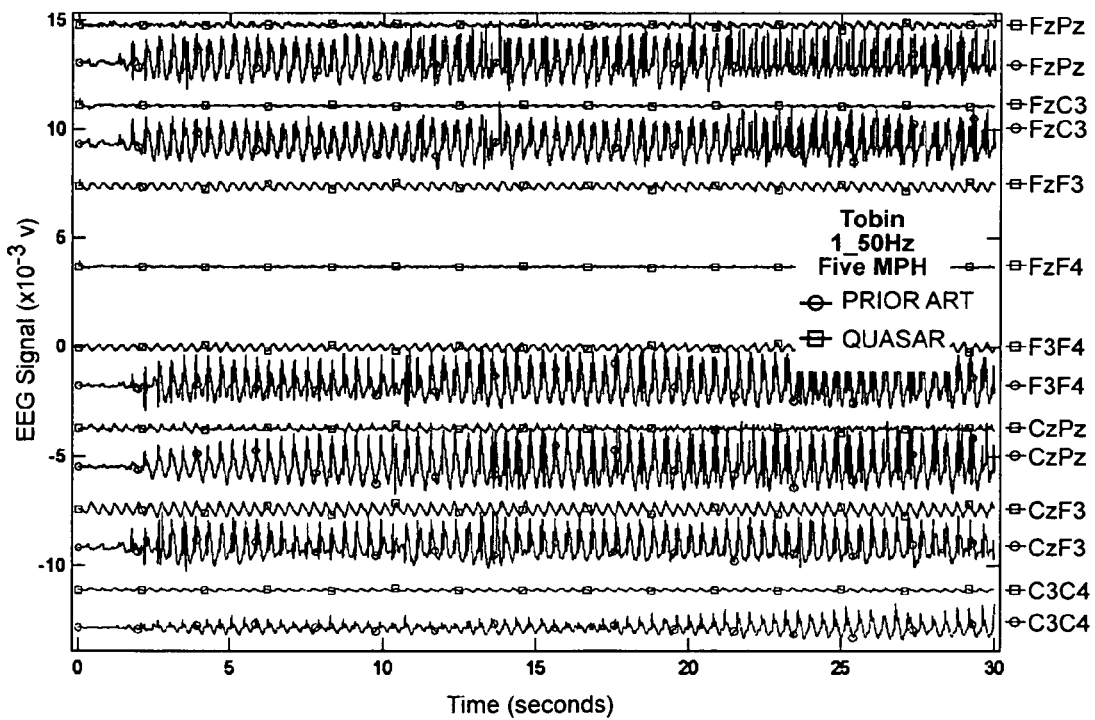
FIG. 8 depicts biopotential data acquired from a sensor mounted within the sensor mounting system of FIG. 7, and the normal range of inertial forces present during use.

A comparison of EEG data collected by mounting system 12' including dry electrodes built according to the invention and enclosed within pod 80 and a system comprised of wet electrodes held against the scalp by a conventional elastic cap is shown in FIG. 8. In these data, the upper trace in each pair of data corresponds to a dry electrode held by a mounting system build according to the invention, while the lower trace of each pair is a conventional set electrode. Note there is no accompanying wet electrode data for the traces marked FzF3 and FzF4. For all data, the subject is running on a treadmill at 5 mph. The ability of the sensor mounting system 12' to isolate sensor 10' from the motion of the subject is clearly visible by the absence of the 2 mV peak to peak motion artifact that begins at time 2 seconds and continues throughout the recording. It should be noted that mounting system 12' built according to the invention utilized dry electrodes, which could not otherwise have functioned at the levels shown.

Although described with reference to preferred embodiments of the invention, it should be readily understood that various changes and/or modifications can be made to the invention without departing from the spirit thereof. For instance, although the main body portions are depicted as cylindrical, other shapes could be utilized. In general, the invention is only intended to be limited by the scope of the following claims.

We claim:

1. A sensor mounting system for use with a subject comprising:
   a rigid mounting pod;
   a rigid main body portion encased in the rigid mounting pod and defining a housing having an opening therein;
   a secondary support structure adapted to retain the rigid mounting pod against and in contact with a subject surface;
   a sensor arranged at the opening of the housing and including an interface element adapted to contact the subject surface;
   a compression element within the housing connecting the sensor to the housing, wherein the compression element provides a biasing force adapted to bias the sensor toward the subject surface, with the biasing force being predetermined to reduce subject discomfort while providing improved coupling between a subject surface and the sensor; and
   a second compression element attaching the rigid main body portion to the rigid mounting pod.

2. The sensor mounting system of claim 1, wherein the sensor is captured in the housing such that it does not extend beyond the rigid main body portion, with the compression element providing the biasing force toward the opening of the housing.

3. The sensor mounting system of claim 1, further comprising means for transferring torque between the rigid main body portion and the sensor.

4. The sensor mounting system of claim 1, in which the compression element has a first spring constant in a direction normal to the opening of the housing and a second spring constant in a direction parallel to the opening of the housing.

5. The sensor mounting system of claim 1, wherein the interface element extends from the sensor in a direction away from the housing.

6. The sensor mounting system of claim 5, wherein the sensor interface element is constituted by a plurality of fingers adapted to sit between strands of hair on the subject surface.

7. The sensor mounting system of claim 6, wherein the plurality of fingers include rounded tips.

8. The sensor mounting system of claim 6, wherein the plurality of fingers include an insulating layer.

9. The sensor mounting system of claim 1, wherein the sensor is selected from the group consisting of a biopotential sensor, a thermal sensor, an acoustic sensor and a thermoelectric generating device.

10. The sensor mounting system of claim 9, wherein the sensor comprises a dry electrode.

11. The sensor mounting system of claim 1, further comprising a metallic conductor incorporated into the rigid main body portion.

12. The sensor mounting system of claim 11, further comprising a metal cover located over the sensor, wherein the metallic conductor is electrically connected to the metal cover.

13. The sensor mounting system of claim 1, further comprising an interface layer extending from the rigid main body portion and adapted to contact the subject surface upon attachment of the sensor mounting system.

14. The sensor mounting system of claim 13, wherein the interface layer takes the form of fingers extending from the rigid main body portion, with the interface layer being adapted to sit between strands of hair on the subject surface.

15. The sensor mounting system of claim 13, wherein the interface layer is a soft material adapted to improve subject comfort.

16. The sensor mounting system of claim 15, wherein the interface layer has a high coefficient of friction to the subject surface.

17. The sensor mounting system of claim 1, further including a secondary sensor.

18. The sensor mounting system of claim 17, wherein the secondary sensor is a displacement sensor adapted to measure sensor contact pressure.

19. The sensor system of claim 1, further comprising: means for permitting both limited linear and rotary movement of the sensor relative to the rigid main housing.

20. A method for mounting a sensor on a subject comprising:
   attaching a sensor mounting system, including: a rigid mounting pod; a rigid main body portion encased in the rigid mounting pod and defining a housing having an opening therein; a secondary support structure adapted to retain the rigid mounting pod against and in contact with a subject surface; a sensor arranged at the opening of the housing and including an interface element adapted to contact the subject surface; a compression element within the housing connecting the sensor to the housing; and a second compression element attaching the rigid main body portion to the rigid mounting pod, to the subject surface with the secondary support structure; and
   biasing the sensor housed within the main body portion of the sensor mounting system against the subject surface by the first compression element attached to the main body portion, wherein the first compression element provides a first predetermined biasing force biasing the sensor toward the subject surface and set to optimize coupling of the sensor with the subject surface while reducing subject discomfort.

21. The method of claim 20, further comprising:
   biasing the rigid main body portion against the subject surface with the secondary support structure, wherein the secondary support structure provides an adjustable biasing force.

22. The method of claim 20, further comprises shifting a plurality of fingers extending from the sensor to enable parting of hair located on the subject surface to enhance sensor contact.

23. The method of claim 20, further comprising:
   attaching the rigid main body portion to the rigid mounting pod of the sensor mounting system via the second compression element;
   attaching the rigid mounting pod to the subject surface with the secondary support structure such that the rigid mounting pod is held against the subject surface by an adjustable biasing force; and
   biasing the rigid main body portion against the subject surface by the second compression element attached to the rigid mounting pod, wherein the second compression element provides a second predetermined biasing force, wherein the second predetermined biasing force of the second compression element is set to optimize coupling of the sensor with the subject surface while reducing subject discomfort.

24. The method of claim 22, wherein the sensor includes a sensor interface element in the form of a plurality of fingers adapted to sit between strands of hair on the subject surface, and the method further comprises rotating the sensor back and forth across the subject surface such that the plurality of fingers part the hair on the subject surface and provide improved contact between the subject surface and the sensor.

* * * * *